United States Patent [19]

Forman

[11] 4,178,934
[45] Dec. 18, 1979

[54] URINE METER AND COLLECTION ASSEMBLY

[75] Inventor: Hugh M. Forman, Waukesha, Wis.

[73] Assignee: G. D. Searle & Co., Skokie, Ill.

[21] Appl. No.: 864,178

[22] Filed: Dec. 27, 1977

[51] Int. Cl.² .............................................. A61R 5/44
[52] U.S. Cl. .................................. 128/295; 128/762; 128/771
[58] Field of Search ............... 128/275, 294, 295, 2 F; D24/52, 54; 248/311.1, 360; 141/382, 388; 4/144.1–144.4, 301, 113.1

[56] References Cited

U.S. PATENT DOCUMENTS

| | | | |
|---|---|---|---|
| 3,383,017 | 5/1968 | Krings | 150/1 |
| 3,683,894 | 8/1972 | Villari | 128/275 |
| 4,000,649 | 1/1977 | Hanifl | 128/2 F |
| 4,019,707 | 4/1977 | Quinn et al. | 128/275 |
| 4,095,589 | 6/1978 | Manschot | 128/2 F |

Primary Examiner—Robert W. Michell
Assistant Examiner—J. L. Kruter
Attorney, Agent, or Firm—James R. Henes; John A. Dhuey

[57] ABSTRACT

A urine meter and collection assembly is described having a rigid, compartmentalized measuring container attached to a flexible wall of the collection bag. The fluid inlet and transfer ports are telescopically aligned to accept the fluid drainage tube and the flexible bag wall is utilized as a hinge during emptying of the measuring container. The telescopic arrangement provides for a compact assembly and minimizes disturbances of the patient drainage line.

9 Claims, 5 Drawing Figures

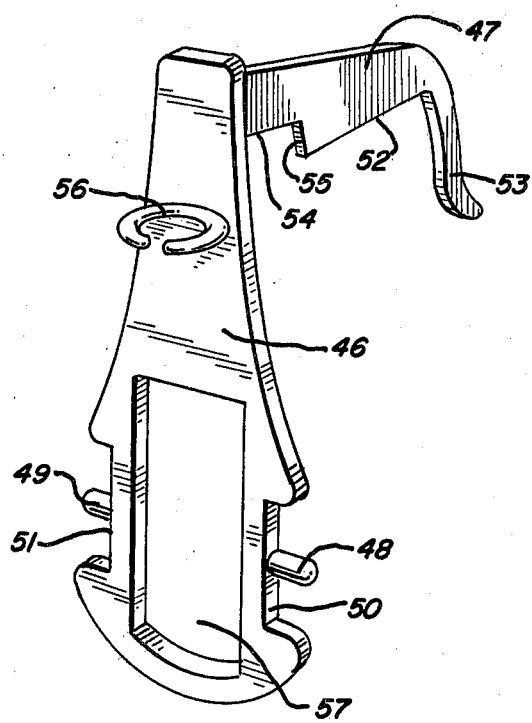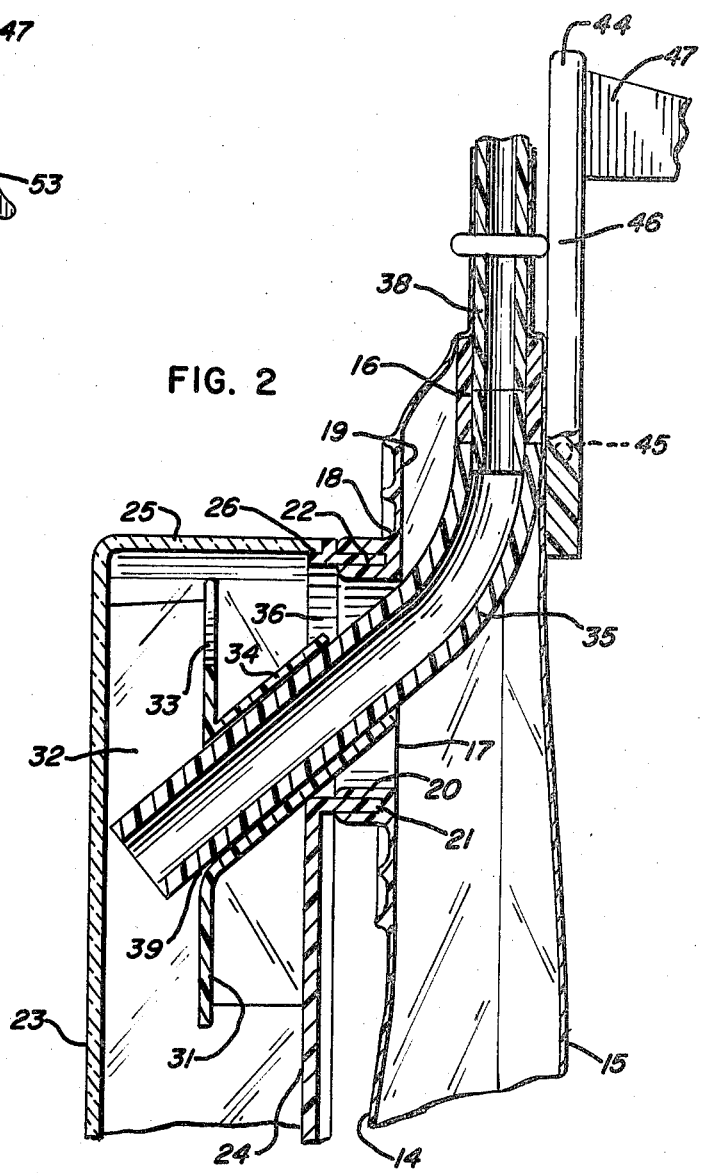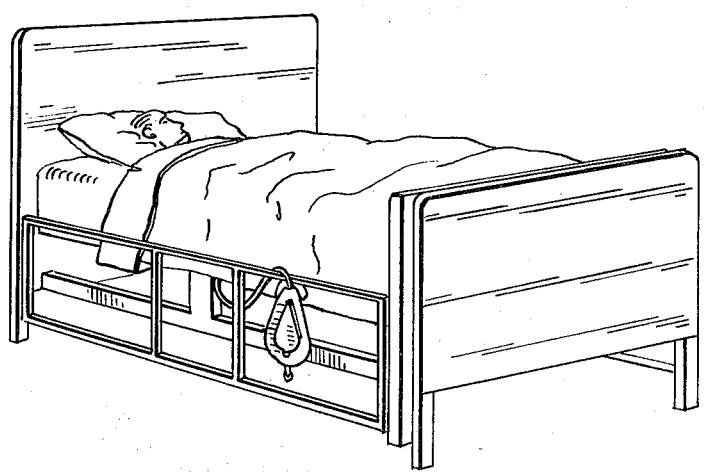

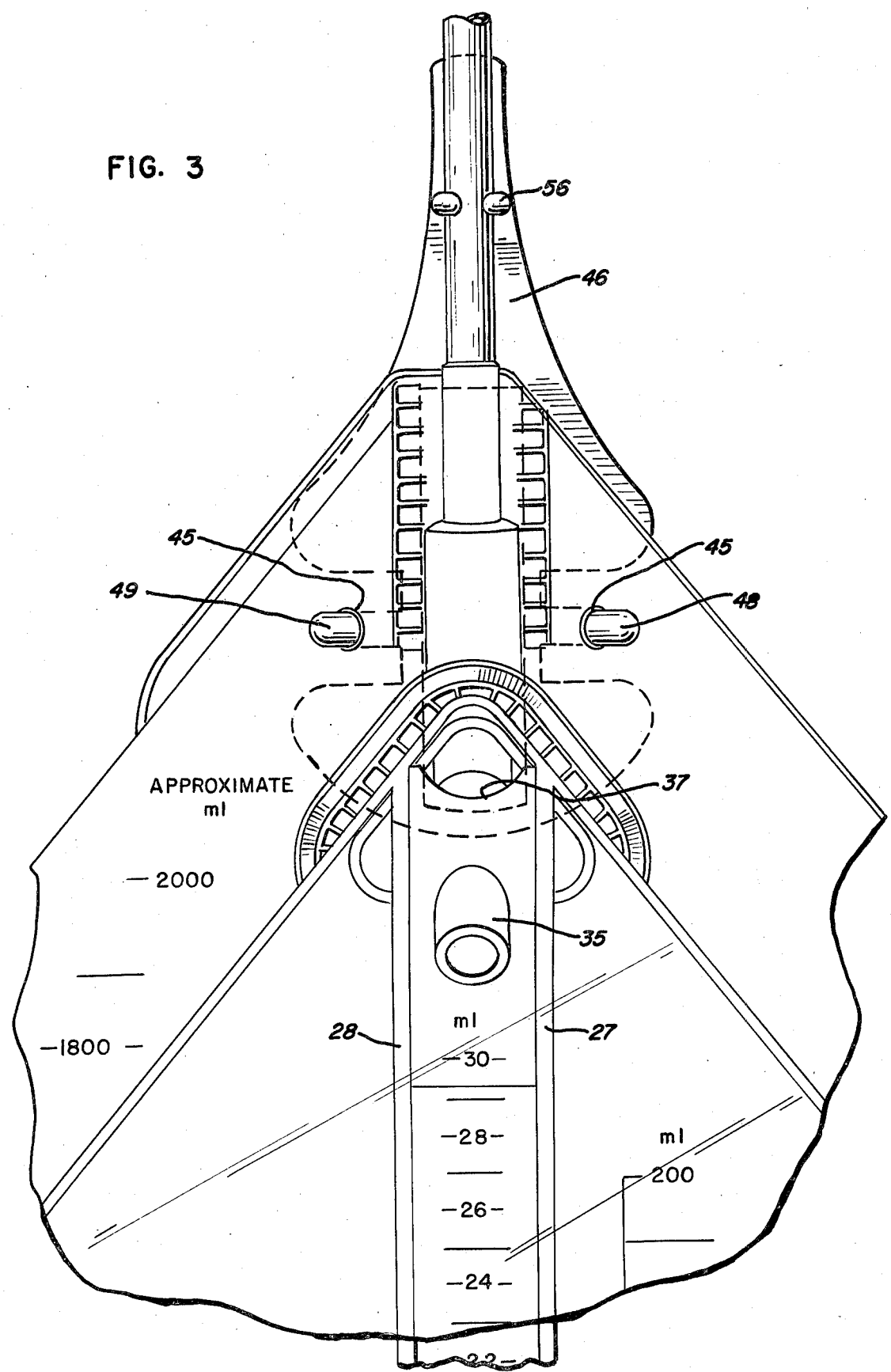

URINE METER AND COLLECTION ASSEMBLY

The present invention is concerned with urological apparatus. More particularly, it is concerned with a urine meter and collection assembly.

In many medical situations it is necessary to monitor fluid output of a patient. In particular, for pediatric patients or in low fluid-output patients having certain types of kidney disease it is imperative that accurate measurements of small volumes be made. At times selected portions of the fluid may be collected to determine if medication is being effective or to supply specimens for sequential laboratory tests.

The use of a urine meter attached to a collection container has been described previously. See for example, U.S. Pat. Nos. 3,683,894 and 3,727,603 and Reissue Patent No. 26,964. However, prior art devices have been deficient in many respects.

Devices as described in U.S. Pat. No. Re 26,964 are not entirely satisfactory since they create a collection apparatus of excessive length. Location of the device near a patient often is impractical or cumbersome at best. The container described in U.S. Pat. No. 3,727,603, being composed of a rigid collection container and a rigid measuring container is difficult to store and also takes up substantial space during use. Overcoming several of these noted deficiencies is the system described in U.S. Pat. No. 3,683,894. Therein a flexible collection bag is described having a rigid measuring container connected to the bag. To empty the measuring container, it is necessary to detach it from the collection bag and raise it to a level above the inlet to the bag. Although seemingly a relatively simple operation, it requires substantial movement of the measuring container filled with fluid and also the inlet drainage tube which is connected to a patient. Dropping of the container can result in spillage and discomfort to the patient if the collection tube is moved excessively.

In order to correct such deficiencies the present invention utilizes telescopically connected containers and compartments and a flexible bag wall as a hinge for and a support of the measuring container. The measuring container is attached directly to the collection container in a preferred embodiment. The telescopic arrangement of the fluid drainage tube and the fluid transfer ports facilitates emptying of the measuring container with minimal disturbance of the drainage tube and provides for an extremely compact configuration.

The invention will be described particularly with reference to the following drawings in which:

FIG. 1 is an overall view of the device as utilized with a patient;

FIG. 2 is a cross-sectional view of the telescopically arranged components;

FIG. 3 is an enlarged front view of the hinged portion of the device;

FIG. 5 is a front view of a preferred bag support.

Figure 4:
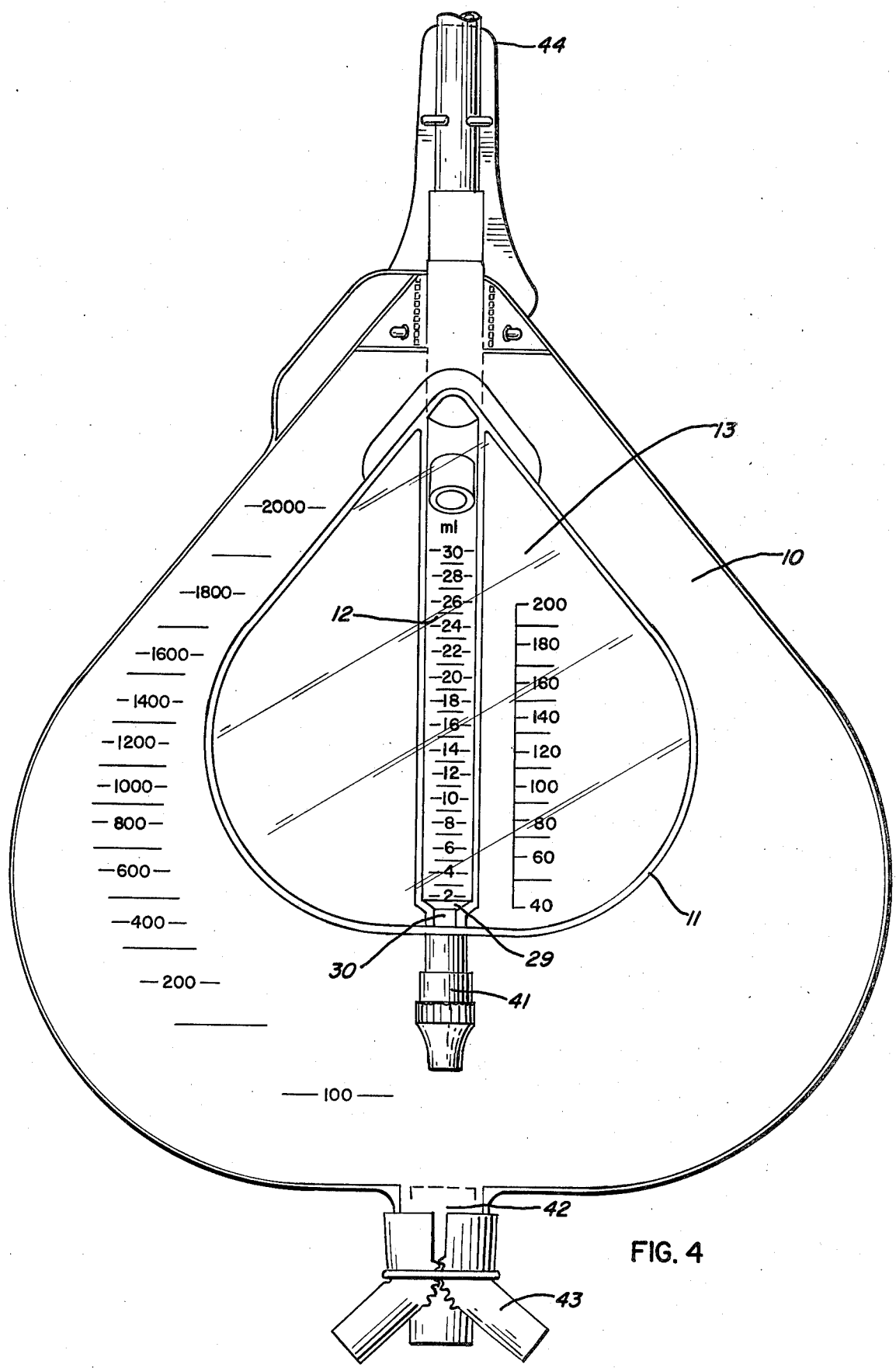
FIG. 4 is an overall front view of the device.

With particular reference to FIGS. 2-4, the measuring and collection assembly comprises a collection container 10 and a measuring container 11. Measuring container 11 is divided onto a first compartment 12 and a second compartment 13. Both collection container 10 and measuring container 11 perferably are tear-drop shaped and connected near their apexes.

Collection container 10 has at least one flexible wall 14 which faces measuring container 11. Preferably both walls of the collection container are flexible to facilitate operating and storing of the devices. Front facing wall 14 and back wall 15 are joined and sealed about their periphery and provided with an inlet port 16 at their uppermost point. At a location below inlet port 16, transfer port 17 is provided in wall 14. Transfer port 17 conveniently is formed with a triangular periphery with its apex located along a vertical line from the central axis of inlet port 16. Surrounding transfer port 17 is flange 18, sealed to flexible wall 14 along mating surface 19. Flange 18 has an outwardly extending portion 20 enclosing a groove 21 which is adapted to receive a corresponding flange member 22 on measuring container 11.

Measuring container 11 is formed with two opposed rigid walls 23 and 24 and outside wall 25. In practice, walls 23 and 25 are transparent and molded in a unitary construction. Wall 24 which may be clear but is preferrable opaque to improve liquid level visibility is separately attached thereto. In its preferred form, wall 24 has a peripheral recessed portion 26 to engage wall 25, which is bonded and sealed to wall 24 with any suitable adhesive or welding system. Wall 24 is molded with integral flange 22, which is retained within groove 21 on flange 20.

Front wall 23 further is molded with inwardly extending walls 27 and 28, botton wall 29 and outlet passage 30. Walls 27 and 28 are vertical and extend substantially the height of container 11. Near the top of container 11, walls 27 and 28 are partially cut away to provide an overflow opening into second compartment 13. Walls 27 and 28 extend across container 11 to divide container 11 into a first compartment 12 and a second compartment 13. Each side of compartment 13 is in fluid communication with the other through the opening under passageway 30 and above the cut out portions of walls 27 and 28.

A fluid deflector and tube guide 31 is attached to the upper portions of walls 27 and 28 to assure complete fluid flow into first compartment 12. Fluid deflector and tube guide 31 consists of a flat portion 33 abutting walls 27 and 28 and an integral tubular portion 34 which is adapted to receive fluid transfer means 35, which conveniently is a section of flexible tubing, e.g. latex tubing. Tubular portion 34 of tube guide 31 extends into transfer port 36 formed in wall 24. Additionally, a recessed portion 37 is provided at the top of guide 31 to provide a vent in the event that fluid enters first compartment 12 very rapidly. Tubular portion 34 effectively prevents the tube 35 from slipping out from compartment 12 when measuring container 11 is inverted for emptying. Flat portion 33 serves as a fluid deflector to prevent backflow and fluid creep into second compartment 13 before first compartment 12 has been filled.

Fluid transfer means 35 is adapted to receive a drainage tube 38 for connection to a patient. When container 11 is inverted during the emptying operation, tube 35 is pinched off to prevent further flow into the measuring container or back up into drainage tube 38. The telescopic arrangement of tube 35 through inlet port 16, transfer ports 17 and 36 into inlet port 39 minimizes interference with the patient tube 38, especially when container 11 is inverted for emptying.

Flexible bag wall 14 is utilized along with flange 18 as a hinging means so that measuring container 11 conveniently can be inverted. When container 11 is inverted, wall 14 flexes and is pulled outwardly near the bottom of flange 18 and flexes inwardly at the top of flange 18.

Since no independent hinging mechanism is required, container 11 can be mounted very near wall 14 to provide a very compact configuration.

The particular shape of containers 10 and 11 is advantageous. The tear-drop shape provides a single point of suspension and inherent vertical positioning for both container 10 and container 11, to facilitate accurate readings since the fluid remains level. The flat configuration of measuring container 11 provided by wide front and back walls and a short side wall minimize fluid level variations across measuring container 11 in a direction perpendicular to the front and back walls. Additionally, the tear-drop shape facilitates complete emptying of container 11 when it is placed in an inverted position.

The telescopic arrangement of transfer port 17, transfer port 36 and fluid transfer tube 35 is further advantageous since no direct vent to the atmosphere is required in measuring container 11. When container 11 is inverted for emptying, an air exchange occurs from collection container 10 to measuring container 11. Odors thus are minimized and bacterial air filters are eliminated.

First compartment 12 conveniently is provided with valve means 41 on outlet 30 so that individual emptying of that container can be accomplished. It often is desirable to collect fresh samples of urine for certain laboratory procedures. Additionally, collection bag 10 can be provided with outlet 42, which is provided with a valve 43.

First compartment 12 generally is formed with a volume less than second compartment 13 to provide different sensitivity in readings. The compartments are calibrated and provided with appropriate measuring indicia.

Collection container 10 perferably is attached to a mounting hook 44 by means of two holes 45 in walls 14 and 15 in collection container 10. Hook 44 comprises a first support member 46 joined to a second support member 47. First support member 46 is of generally planar configuration and is adapted to attach to and support container 10 by means of members 48 and 49 which are adapted to be inserted in holes 45 in container 10. Members 48 and 49 preferably are rod-like shaped appendages extending outwardly from support member 46 and located within recess 50 and 51 to accomodate the bulk of container 10 which extends about members 48 and 49 when members 48 and 49 are inserted into holes 45.

A second support member 47 is joined to the end of first support member 46 which is remote from the bag attachment means. Member 47 is adapted to attach to or be supported by other means in the patient environment which will provide a stationary support for the entire fluid collection assembly. Those other means, for example, may be a piece of room furniture, a collection stand or most conventionally the patient's bed rail. The rails on the patient's bed provide a most convenient location for the placement of the collection apparatus since it is stationary, near the patient and generally out of the flow of normal activity in the patient's room.

Member 47 is formed with at least one horizontal flat portion 52 and one downwardly extending portion 53. Flat portion 52 is adapted to rest on the top of the patient's bed rail and portion 53 extends downwardly from the bed rail on the inboard side of the bed. Additional flat and downwardly extending portions such as exemplified by portions 54 and 55, respectively, can be provided with dimensions different from portions 52 and 53 to accomodate differently sized bed rails.

Hook means 44 can be formed with a tube retainer 56 on the face of member 46 which is opposite from member 47. Conveniently retainer 56 is a C-shaped ring appropriately sized to accept the drainage tubing. An opening 57 in member 46 can be provided to accomodate the bulk of the collection container 10 and attached tubing which resides in the area of attachment to hook 44. That arrangement facilitates hanging of the assembly in a vertical position.

Alternatively, collection container 10 can be attached in a conventional manner to a support member attached to wall 15 and adapted to engage a conventional hook means for attachment to a bed member near a patient. Such a configuration preserves the single point suspension of the entire system.

Although the invention has been described with reference to the preferred embodiment illustrated in the drawings, many modifications will be apparent to those skilled in the art without departing from the spirit or scope of this invention.

What is claimed is:

1. A urine metering and collection assembly comprising:
   a fluid collection container having at least one flexible wall, a first inlet port near the top end of said container and a transfer port in said flexible wall below said inlet port;
   a rigid measuring container having at least one first volume calibrated compartment, said first volume calibrated compartment, having a second inlet port;
   means for attaching said measuring container to said flexible wall, said means aligning said transfer port and said second inlet port; and
   a flexible tubular conduit continuously extending from said first inlet port, through said transfer port and into said second inlet port to deliver fluid from said first inlet port to said second inlet port.

2. An assembly as in claim 1 wherein said measuring container has a second volume calibrated compartment, said first compartment being of a lesser volume than said second compartment and being contained within said second compartment, and said second compartment having a second transfer port in substantial alignment with said first transfer port and said second inlet port.

3. An assembly as in claim 2 wherein said tubular conduit extends through said first inlet port and each of said transfer ports into said second inlet port.

4. An assembly as in claim 2 further comprising overflow means associated with said first compartment for transfering fluid from said first compartment to said second compartment.

5. An assembly as in claim 4 wherein said fluid collection container is of tear-dropped shape, said measuring container is a tear-dropped shape, said first compartment is substantially rectangular and located at the center of said measuring container, said first inlet port being located at the top of said collection container, said first transfer port located below said first inlet port near the top of said container, said second transfer port being opposed to said first transfer port, and said second inlet port located at the top of said first compartment.

6. An assembly as in claim 5 wherein said attachment means comprises a generally triangular upstanding flange on said flexible wall surrounding said first transfer port and an outwardly extending flange surrounding said second transfer port on said measuring container sealed to said upstanding flange.

7. An assembly as in claim 5 further comprising tube guide means attached to said top portion of said first compartment.

8. An assembly as in claim 7 further comprising valving means on the bottom of said first compartment.

9. An assembly as in claim 7 wherein said tube guide means includes a fluid deflector plate.

* * * * *